United States Patent [19]

Eggers

[11] 4,013,409

[45] Mar. 22, 1977

[54] 5-HYDROXYMETHYL-1-AZA-3,7-DIOX-ABICYCLO[3.3.0]-OCTANE AS A SETTING AGENT FOR PERMANENT WAVING

[75] Inventor: Warren J. Eggers, Aurora, Ill.

[73] Assignee: IMC Chemical Group, Inc., Terre Haute, Ind.

[22] Filed: June 23, 1975

[21] Appl. No.: 589,290

[52] U.S. Cl. .................................. 8/127.51; 132/7; 424/71; 424/72

[51] Int. Cl.$^2$ ......................................... A61K 7/09

[58] Field of Search ............ 260/307 F; 424/71, 72; 8/127.51; 132/7

[56] References Cited

UNITED STATES PATENTS

| 2,363,465 | 11/1944 | Senkus | 260/584 R |
|---|---|---|---|
| 2,363,466 | 11/1944 | Senkus | 260/584 R |
| 3,248,285 | 4/1966 | Berke | 424/71 X |

OTHER PUBLICATIONS

Chemistry and use of Aminohydroxy Compounds, Commercial Solvents Corporation, New York, (1972), pp. 24 and 25.

*Primary Examiner*—Albert T. Meyers
*Assistant Examiner*—Vera C. Clarke
*Attorney, Agent, or Firm*—Robert H. Dewey; Howard E. Post

[57] ABSTRACT

A method of setting keratin fibers which have been treated with a thiol reducing agent by treating said fibers with an oxazolidine.

4 Claims, No Drawings

5-HYDROXYMETHYL-1-AZA-3,7-DIOXABICY-CLO[3.3.0]-OCTANE AS A SETTING AGENT FOR PERMANENT WAVING

BACKGROUND OF THE INVENTION

This invention relates to a setting composition for permanent wave operation. In a particular aspect this invention relates to a method of setting keratinic fibers which have been treated with a thiol reducing agent.

It is known that a convenient method for permanently waving keratinic fibers, and particularly hair, consists in a first stage operation wherein the S—S linkages of the keratin fiber are opened with the aid of a reducing agent, such as thiol, at an alkaline pH. Thereafter, the hair is rinsed and subsequently treated in a second stage operation with an oxidizing or neutralizing agent, i.e. a setting agent, to reconstitute the S—S bridges or linkages of the keratin so as to impart to the hair the desired configuration or style.

SUMMARY OF THE INVENTION

It is an object of this invention to provide a setting composition for permanent wave operation.

It is another object of this invention to provide a method of setting keratinic fibers which have been treated with a thiol reducing agent.

It is yet another object of this invention to provide a method of semi-permanently waving keratinic fibers without previously treating the fibers with a thiol reducing agent.

Other objects of this invention will be apparent to those skilled in the art from the description herein.

It is the discovery of this invention that 5-hydroxymethyl-1-aza-3,7-dioxobicyclo[3.3.0] octane, hereinafter designated Oxazolidine-T, is an effective setting agent for keratinic fibers which have been treated with a thiol reducing agent and makes possible a method for setting said fibers by the steps of (a) applying to said fibers said Oxazolidine-T as an aqueous solution containing from about 5% to about 15% Oxazolidine-T, (b) maintaining contact of said solution with said fiber for about 1–10 min., and (c) rinsing said solution from said fiber.

DETAILED DISCUSSION

The chemistry involved in the practice of the present invention is obscure. As stated above, the first stage of the permanent waving operation involves opening the S—S linkage of the keratinic fiber with a suitable agent, usually a thiol, of which a large number can be used. Ammonium thioglycolate is a widely used agent for this purpose. Previously an oxidizing agent has been employed to restore the S—S linkage, i.e. to "neutralize" the effect of the thiol compound, although no direct reaction necessarily occurs between the "neutralizer" and the thiol compound. However Oxazolidine-T is not known to be an oxidizing agent and its role in restoring or possibly substituting for the S—S linkage has not been elucidated. Accordingly it is preferred to refer to this action as a "setting" action rather than a neutralizing action and to refer to the Oxazolidine-T solution as a setting agent rather than a neutralizing agent.

In general, the Oxazolidine-T is used in the same manner previously employed for the prior art peroxides. The permanent waving process does not lend itself to quantitative limits. A composition is prepared containing from about 5% to about 15%, preferably about 10%, of Oxazolidine-T dissolved in water. The composition can also contain a thickening agent such as carboxymethyl cellulose, hydroxymethyl cellulose or a wax. Further the composition can also contain certain other conventional cosmetic adjuvants such as a perfume, dyes, stabilizers, preservatives, quaternary ammonium compounds, non-ionic compounds or anionic compounds. These adjuvants are preferably introduced into the liquid Oxazolidine-T solution. The composition is padded on to the hair curl in an amount just under that which is sufficient to result in a small amount of run-off. The solution and curl are allowed to remain in contact for several minutes, then the curler is removed. Preferably, the Oxazolidine-T composition is then once again padded onto the curl until it is well soaked. After standing several minutes, the Oxazolidine-T composition is rinsed from the hair with water. The hair can then be again rolled onto the curlers and be permitted to dry.

The Oxazolidine-T of the present invention is commercially available and the usual commercial product is suitable for use. It can also be readily prepared from tris(hydroxymethyl)aminomethane and formaldehyde as is known in the art, e.g. see Wm. B. Johnston, U.S. Pat. No. 2,448,890. It is used at a concentration of about 5% to about 15% or more, preferably at about 10%.

Oxazolidine-T is a relatively innocuous material. It caused no significant change in the eyes of test rabbits when 100 mg was introduced under the lower eyelid, which was held closed until the Oxazolidine-T dissolved. The cornea and iris were normal 24, 48 and 72 hours after exposure and the eyes were free from chemosis and redness. The product is also practically harmless on acute oral administration. No deaths occurred at a single dose of 2500 mg/kg, the highest dosage attempted.

As mentioned previously, the premanent waving operation is a 2-stage process. The present invention is intended to substitute for the second stage of the previous operation, irrespective of the thiol compound used in the first stage. Hence it is deemed that a discussion of the first stage is inappropriate here. However as a typical example of a stage 1 step, it can be mentioned that the hair, preferably cleaned of oils and dirt, is rolled onto hair waving rollers and treated with a composition such as:

| | |
|---|---|
| Thioglycolic acid | 8 g |
| Ammonia, q.s.p. neutralization | |
| Monoethanolamine | 4.5 g |
| Dye | 0.2 g |
| Perfume | 0.1 g |
| Water, q.s.p. | 100 cc. |

After a suitable waiting period to allow the S—S linkage to be reduced, the hair is thoroughly rinsed with water. It is now ready for the second stage, e.g. the treatment with Oxazolidine-T.

The Oxazolidine-T composition is also useful as a semi-permanent hair setting agent. This type of hair waving operation is a one-stage process which does not involve the reduction-neutralization steps of 2-stage process. In the semi-permanent process, the hair is thoroughly wetted or soaked with the setting agent then is rolled up on the hairwaving curlers. Under commercial conditions, steam is applied by a special apparatus to the curled hair for a suitable length of time. It is then washed to remove the setting agent, dried and is ready for combing out.

The invention will be better understood by reference to the following examples. It is understood, however, that the examples are intended only for illustration and it is not intended that the invention be limited thereby.

EXAMPLE 1

A sample of medium brown virgin (nontreated) hair was wet with water and rolled on a small plastic curler. Ammonium thioglycolate waving lotion was applied liberally to the hair on the curler. The lotion used was a commercial preparation from the Toni Home Permanent kit, marketed by the Gillette Co. The waving lotion was allowed to remain on the hair for 20 minutes and it was then rinsed with 120° F water and towel blotted. The curl was saturated with a setting agent comprising a 10% aqueous solution of Oxazolidine-T for 2 minutes. The hair was carefully removed from the plastic curler and again soaked with the setting agent. Each lock of hair was thoroughly rinsed with 120° F water. The hair was again rolled on clean plastic curlers and allowed to dry overnight. On the following day, the lock of hair was removed from the curler and examined for appearance, which was excellent. On the next day, the curl of hair was thoroughly wet with water and again rolled on a clean plastic curler. After overnight dry, the hair was removed from the curler and examined for appearance, which again was excellent. The curl was then placed in a bell jar containing a pan of warm water overnight. This test was for the purpose of evaluating the curl under humid conditions. The result was excellent.

The foregoing experiment was repeated in all essential details except that the setting agent used was a commercial hydrogen peroxide solution marketed by the Toni Co. and intended for use in the home. The hair neutralized with the Oxazolidine-T was fully equivalent in all respects to the hair neutralized with the peroxide, and it was superior at the end of the humidity test.

EXAMPLE 2

The experiment of Example 1 was repeated in all essential details except that a setting agent composition comprising a 5% solution of Oxazolidine-T was substituted for the 10% solution. The hair set with the 5% solution was fully equivalent to the hair set with the 10% solution except at the end of the humidity test at which time the curl was inferior in quality to both that from the 10% Oxazolidine-T solution and from the commercial peroxide preparation.

EXAMPLE 3

A swatch of virgin hair (undyed, untreated hair) was cut into ten convenient locks for curling. Samples of hair were treated by soaking for 12 minutes in each of the solutions listed below:
1. 5% aqueous solution of Oxazolidine-T
2. 10% aqueous solution of Oxazolidine-T
3. 5% aqueous ammonia solution
4. 10% aqueous ammonia solution
5. Final Net, a commercial semi-permanent hair setting lotion manufactured by the Clairol Company of Stamford, Connecticut.

After soaking, the hair was curled on light weight aluminum brush curlers. The set hair was then placed in a 212° F oven for 30 minutes, simulating the commercially available steam set apparatus. After 30 minutes the set hair was removed from the oven and the hair was taken off the curler with the following results: All five samples of hair curled equally. The curls, identified below by the treatment solution, were rated as follows for texture, 1 being the softest and 5 being the stiffest.
1. 5% Oxazolidine-T
2. 5% ammonia
3. 10% Oxazolidine-T
4. 10% ammonia
5. Final Net After the above rating, the hair curls were combed and the appearance was rated as follows (again, the curls are identified by the treatment solution applied), 1 being the best, and 5 being the worst:
1. 10% Oxazolidine-T
2. 5% ammonia
3. 5% Oxazolidine-T
4. 10% ammonia
5. Final Net After evaluating the combed hair, it was thoroughly rinsed in warm water and hung to dry at room temperature. After 16 hours the hair samples were rated as follows for degree of curl:
1. 5% ammonia - best
2. 10% Oxazolidine-T
3. 5% Oxazolidine-T
4. 10% ammonia
5. Final Net - worst The following day the hair samples were placed in a bell jar containing a pan of water to test for the effect that humidity would have on the curl. After 16 hours, the following results were obtained with relation to degree of curl:
1. 5% ammonia - best
2. 10% Oxazolidine-T
3. 5% Oxazolidine-T
4. 10% ammonia
5. Final Net - worst The hair was hung in the laboratory for seven days and then thoroughly washed with a shampoo, towel dried and hung in the laboratory overnight. All five samples of hair were completely straight, free from curl and of equally soft texture. This completed the test showing that Oxazolidine-T is useful as a semi-permanent hair setting lotion.

Oxazolidine-T contributes better curl properties than either ammonia or the Final Net setting lotion. The Oxazolidine-T treated hair has the advantage of less stiffness than the Final Net. The ammonia solution also is a semi-permenent setting lotion, but due to its strong odor and high pH, as indicated in the following table, would be less suitable than the Oxazolidine-T.

| Solution | pH |
|---|---|
| 10% Oxazolidine- | 8.4 |
| 5% Oxazolidine-T | 8.55 |
| Final Net | 6.00 |
| 10% ammonia | 11.55 |
| 5% ammonia | 11.35 |

I claim:
1. A method for treating keratinic fiber which has been treated with a thiol reducing compound comprising the steps of applying to said fiber an effective amount of a 5–15% by weight aqueous solution of -5- hydroxymethyl-1-aza-3,7-dioxabicyclo[3.3.0] octane, rinsing with water and drying said fiber.

2. The method of claim 1 wherein the concentration of 5-hydroxymethyl-1-aza-3,7-dioxabicyclo[3.3.0]-octane is about 5% by weight.

3. The method of claim 1 wherein the concentration of 5-hydroxymethyl-1-aza-3,7-dioxabicyclo[3.3.0]-octane is about 10% by weight.

4. In a two-stage operation for permanent waving of hair wherein the hair is treated with a reducing agent in the first stage and a setting agent in the second stage, the improvement consisting of using as the setting agent an aqueous solution of 5-hydroxymethyl-1-aza-3,7-dioxabicyclo[3.3.0] octane in a concentration of about 5–15% by weight.

* * * * *

UNITED STATES PATENT OFFICE
CERTIFICATE OF CORRECTION

Patent No. 4,013,409          Dated March 22, 1977

Inventor(s) Warren J. Eggers

It is certified that error appears in the above-identified patent and that said Letters Patent are hereby corrected as shown below:

Column 2, line 38, "premanent" should read -- permanent --

Column 4, line 53, "permenent" should read -- permanent --

Column 4, line 58, "Oxazolidine" should read
         -- Oxazolidine-T --

Signed and Sealed this nineteenth Day of July 1977

[SEAL]

Attest:

RUTH C. MASON
Attesting Officer

C. MARSHALL DANN
Commissioner of Patents and Trademarks